United States Patent [19]

Scholz et al.

[11] Patent Number: 5,027,803
[45] Date of Patent: Jul. 2, 1991

[54] ORTHOPEDIC SPLINTING AND CASTING ARTICLE

[75] Inventors: Matthew T. Scholz, Woodbury; Russell D. Birkholz, Oakdale, both of Minn.

[73] Assignee: Minnesota Mining & Manufacturing Company, Saint Paul, Minn.

[21] Appl. No.: 223,105

[22] Filed: Jul. 22, 1988

[51] Int. Cl.$^5$ .............................................. A61F 5/04
[52] U.S. Cl. ................................. 128/89 R; 128/90; 128/91 R
[58] Field of Search .............. 128/90, 91 R, 155, 156, 128/89 R, 87 R; 428/289

[56] References Cited

U.S. PATENT DOCUMENTS

| | | | |
|---|---|---|---|
| 3,421,501 | 1/1969 | Beightol | 128/90 |
| 3,763,858 | 10/1973 | Buese | 128/156 |
| 3,916,887 | 11/1975 | Kelly | 128/851 |
| 3,944,688 | 3/1976 | Inman | 427/381 |
| 3,956,553 | 5/1976 | Palmer et al. | 428/90 |
| 4,108,169 | 8/1978 | Parker | 128/89 R |
| 4,136,687 | 1/1979 | Dabroski | 128/91 R |
| 4,204,532 | 5/1980 | Lind | 128/849 |
| 4,235,228 | 11/1980 | Gaylord, Jr. | 128/91 R |
| 4,273,115 | 6/1981 | Holland | 128/90 |
| 4,320,750 | 3/1982 | Dabroski | 128/91 R |
| 4,344,999 | 8/1982 | Gohlke | 428/212 |
| 4,350,246 | 9/1982 | Mayer | 206/210 |
| 4,362,762 | 12/1982 | Linquist | 128/91 R |
| 4,411,928 | 10/1983 | Baldwin | 427/2 |
| 4,442,833 | 4/1984 | Dahlen | 128/90 |
| 4,467,013 | 8/1984 | Baldwin | 428/289 |
| 4,537,184 | 8/1985 | Williams, Jr. | 128/90 |
| 4,618,524 | 10/1986 | Greitasch et al. | 428/198 |
| 4,628,917 | 12/1986 | Campagna | 128/90 |
| 4,657,804 | 4/1987 | Mays et al. | 428/212 |
| 4,667,661 | 5/1987 | Scholz | 128/90 |
| 4,705,712 | 11/1987 | Cashaw et al. | 428/152 |
| 4,725,481 | 2/1988 | Ostapohenko | 428/213 |

Primary Examiner—Robert A. Hafer
Assistant Examiner—Michael Brown
Attorney, Agent, or Firm—Wegner, Cantor, Mueller & Player

[57] ABSTRACT

Disclosed is an orthopedic article adapted to immobilize a body part having a flexible substrate having opposing surfaces impregnated with a curable compound, and a cover having a flexible sheet and a fluorochemical or a silicone disposed on the surfaces that is permeable to water and impermeable to the curable compound.

20 Claims, 2 Drawing Sheets

ORTHOPEDIC SPLINTING AND CASTING ARTICLE

BACKGROUND OF THE INVENTION

Splinting and casting articles for orthopedic purposes such as immobilization of body parts typically are constructed from porous fabrics that are coated or impregnated with plaster of paris or curable resins. Most of the curable resin systems and the plaster of paris systems are cured or rigidified by exposure to water or aqueous catalyst systems.

Once applied to the patient an effective orthopedic article must provide sufficient strength to protect the immobilized body part. It is also desirable that it be light weight, easy to apply, resistant to degradation due to environmental conditions, particularly water, relatively fast and convenient to cure and sufficiently breathable to allow good oxygen transport and transmission of volatile materials from the skin.

When using orthopedic articles systems which are cured by water or water activated catalysts, it is desirable and necessary to allow ready access to the casting system by water in order to obtain both rapid and complete cure. On the other hand, it is desirable that once cured, the orthopedic article dry as rapidly and completely as possible and be relatively insensitive to water, so as to allow bathing and discretionary exposure to water. It is also desirable that the dried orthopedic article provide improved breathability and porosity to minimize the exposure of the skin under the cast to a continuing moist environment.

The present invention provides for the first time a unitary, ready to apply splinting or casting article which combines the advantages of a porous exterior covering layer and yet protects the skin from leakage of the resin impregnated into the casting material.

The present invention provides an improved orthopedic splinting or casting article which cures rapidly and which has an exterior covering layer. The exterior covering layer has a low surface energy and a porosity sufficient to be breathable while not allowing leakage of its contents. The low surface energy exterior is provided by treatment of the exterior layer of the article, with, for example, a suitable chemical such as a fluorochemical or a silicone. The orthopedic article is constructed of a flexible or moldable substrate that is impregnated with a compound that cures the substrate into an inflexible, load-bearing surface. In the context of this application, "a flexible substrate that is impregnated with a curable compound" is equivalent to "a casting material". Preferably, the article is unitary and comprises a water activated resinimpregnated structural member and a porous exterior covering layer. The cure rate of the resin-impregnated structural member can be adjusted to be faster or slower, while providing improved breathability and improved water-repellency to the article.

In general, casting materials currently available which are constructed of resins impregnated into a sheet comprise resins with surface tensions lower than water. The surface tension of the exterior surface of the orthopedic article of this application is significantly lower than water and known resins and therefore the article is water repellent.

It is also an object of the invention to provide a very porous orthopedic splinting or casting article with improved handleability, e.g., which may be handled without protective gloves. The casting resin is enclosed by a low surface energy exterior layer having a porosity that provides excellent containment of the resin before cure. This means that the liquid curable resin does not migrate through the porous exterior covering layer, thereby providing an article with improved storage stability.

DETAILED DESCRIPTION OF THE INVENTION

This application relates to an improved porous orthopedic splinting and casting article and a method for imparting oil and water repellency to such articles. This application also relates to strong and light-weight orthopedic devices with excellent porosity and stability.

Figure 1:
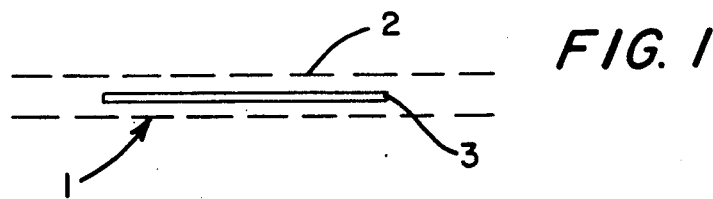
FIG. 1 shows a casting system 1 of the invention wherein a low surface energy layer 2 surrounds a resinimpregnated member 3.

In the method of the present invention oil-repellency and water repellency are imparted to casting articles by a chemical treatment which provides low surface energy to the exposed surface of the article. It has been found that this can be done with articles having very high porosity without inhibiting adequate cure since such articles require exposure to an aqueous environment to effect a cure. As shown in FIG. 1, the orthopedic article of this application generally consists of a flexible substrate 3 that is impregnated with a curable compound, and a water-permeable envelope 2 that surrounds the substrate. Suitable envelopes include water-permeable microporous woven, knitted, non-woven or melt blown layers such as weft knitted tubular fabric, knitted stockinet, non-woven polymeric webs of many types such as polyesters, polyurethanes, nylons or polyolefins, foams, various natural and synthetic woven fabrics such as cotton or synthetic polymeric fabrics such as polyesters, nylons and the like, including spun laced fabrics. These materials may be of high or low modulus but are preferably in a configuration which facilitates conformability and should therefore be drapable, and preferably extensible. The covering material may also be heat sealable.

Water-permeable materials as used herein refer to materials having porosity to both water vapor and liquid.

Suitable fluorochemicals for use to obtain low surface energy layers include any of the fluorochemicals known to those skilled in the art to provide oil-repellency and optionally water repellency to natural or synthetic fibers and films. In general, fluorochemical agents or compositions useful in this invention comprise fluorochemical compounds or polymers containing fluoroaliphatic radicals or groups, Rf.

The fluoroaliphatic radical, Rf, is a fluorinated, stable, inert, non-polar, preferably saturated, monovalent moiety which is both hydrophobic and oleophobic. It can be straight chain, branched chain, or, if sufficiently large, cyclic, or combinations thereof, such as alkylcycloaliphatic radicals. The skeletal chain in the fluoroaliphatic radical can include catenary divalent oxygen atoms and/or trivalent nitrogen atoms bonded only to carbon atoms. Generally Rf will have 3 to 20 carbon atoms, preferably 6 to about 12 carbon atoms, and will contain about 40 to 78 weight percent, preferably 50 to 78 weight percent, carbon-bound fluorine. The terminal portion of the Rf group has at least one trifluoromethyl group, and preferably has a terminal group of at least three fully fluorinated carbon atoms, e.g., $CF_3CF_2CF_2-$. The preferred Rf groups are fully or substantially fluorinated, as in the case where Rf is perfluoroalkyl, $C_nF_{2n+1}-$. Classes of fluorochemical agents or compositions useful in this invention include compounds and polymers containing one or more fluoroaliphatic radicals, Rf. Examples of such compounds include, for example, fluorochemical urethanes, ureas, esters, amines (and salts thereof), amides, acids (and salts thereof), carbodiimides, guanidines, allophanates, biurets, and compounds containing two or more of these groups, as well as blends of these compounds.

Useful fluorochemical polymers containing Rf radicals include copolymers of fluorochemical acrylate and/or methacrylate monomers with co-polymerizable monomers, including fluorine-containing and fluorine-free monomers, such as methyl methacrylate, butyl acrylate, octadecyl methacrylate, acrylate and methacrylate esters of poly(oxyalkylene) polyol oligomers and polymers, e.g., poly(oxyethylene) glycol dimethacrylate, glycidyl methacrylate, ethylene, vinyl acetate, vinyl chloride, vinylidene chloride, vinylidene fluoride, acrylonitrile, vinyl chloroacetate, isoprene, chloroprene, styrene, butadiene, vinylpyridine, vinyl alkyl esters, vinyl alkyl ketones, acrylic and methacrylic acid, 2-hydroxyethyl acrylate, N-methylolacrylamide, 2-(N,N,N-trimethylammonium)ethyl methacrylate and the like.

The relative amounts of various comonomers which can be used with fluorochemical monomer will generally be selected empirically, and will depend on the substrate to be treated, the properties desired from the fluorochemical treatment, i.e., the degree of oil and/or water repellency desired, and the mode of application to the substrate.

Useful fluorochemical agents or compositions include blends of the various classes of fluorochemical compounds and/or polymers described above. Also, blends of these fluorochemical compounds or polymers with fluorine-free compounds, e.g., N-acyl aziridines, or fluorine-free polymers, e.g., polyacrylates such as poly(methyl methacrylate) and poly(methyl methacrylate-co-decyl acrylate), polysiloxanes and the like.

The fluorochemical agents or compositions can include non-interfering adjuvants such as wetting agents, emulsifiers, solvents (aqueous and organic), dyes, biocides, fillers, catalysts, curing agents and the like.

The final fluorochemical agent or composition should contain, on a solids basis, at least about 5 weight percent, preferably at least about 10 weight percent carbon-bound fluorine in the form of said Rf groups in order to impart the benefits described in this invention.

Such fluorochemicals are generally known and commercially available as perfluoroaliphatic group bearing water/oil repellent agents which contain at least 5 percent by weight of fluorine, preferably 7 to 12 percent of fluorine in the available formulations.

As specifically known formulations, the following examples are named:

By the reaction of the perfluoroaliphatic thioglycols with diisocyanates, there results perfluoroaliphatic group-bearing polyurethanes. These products are normally applied in aqueous dispersion for fiber treatment. Such reaction products are e.g. described in U.S. Pat. No. 4,054,592.

Another group of suitable compounds are perfluoroaliphatic group-bearing N-methylol condensation products. These compounds are described in U.S. Pat. No. 4,477,498, where the emulsification of such products is dealt with in detail.

The perfluoroaliphatic group-bearing polycarbodimides are, e.g., obtained by reaction of perfluoroaliphatic sulfonamide alkanols with polyisocyanates in the presence of suitable catalysts. This class of compounds can be used by itself, but often is used with other Rf-group bearing compounds, especially with (co)polymers. Thus, another group of compounds which can be used in dispersions is mentioned. Among these compounds all known polymers bearing fluoroaliphatic residues can be used, also condensation polymers, such as polyesters and polyamides which contain the corresponding perfluoroaliphatic groups, are considered but especially (co)polymers on the basis of e.g. Rf-acrylates and Rf-methacrylates, which can contain different fluorine-free vinyl compounds as comonomers. In DE-A 2 310 801 (see also GB-A 1.413.051/052), these compounds are discussed in detail. The manufacture of Rf-group bearing polycarbodiimides as well as the combination of these compounds with each other is also described in detail.

Besides the aforementioned perfluoroaliphatic group-bearing agents, further fluorochemical components may be used, for example, Rf-group-bearing guanidines, U.S. Pat. No. 4,540,479, Rf-group-bearing allophanates, U.S. Pat. No. 4,606,737 and Rf-group-bearing biurets, U.S. Pat. No. 4,668,406. These classes are mostly used in combination. Others include fluoralkyl-substituted siloxanes, e.g., $CF_3(CF_2)_6CH_2O(CH_2)_3Si(OC_2H_5)_3$.

The useful compounds show, in general, one or more perfluoroaliphatic residues with preferably at least 4 carbon atoms, especially 6 to 14 atoms each.

An exemplary preferred fluorochemical is a formulation of 70% solvents and 30% emulsified solid fluorochemical polymers. The formulation includes as solvents 11% methyl isobutyl ketone, 6% ethylene glycol and 53% water. The fluorochemical polymers are a 50/50 blend of 5/95 copolymer of butyl acrylate and $C_8F_{17}SO_2N(CH_3)C_2H_4OCOCH=CH_2$ prepared as described in U.S. Pat. 3,816,229, incorporated herein by reference (see particularly column 3, lines 66–68 and column 4, lines 1–11) for a 10/90 copolymer. The second component of the 50/50 blend is a copolymer prepared from 1 mole of a tri-functional phenyl isocyanate (available from Upjohn Company under the name PAPI), 2 moles of $C_8F_{17}N(CH_2CH_3)CH_2CH_2OH$ and 1 mole of stearyl alcohol prepared as described in U.S. Pat. 4,401,780, incorporated herein by reference (see particularly Table I, C2 under footnote A). Emulsifiers used are conventional commercially available materials such as polyethoxylated quaternary ammonium compounds (available under the name 5% Ethoquad 18/25) and 7.5% of a 50/50 mixture of $C_8F_{17}SO_2NHC_3H_6N(CH_3)_3Cl$ and a polyethoxylated sorbitan monooleate (available from ICI Limited under the name Tween 80). Such fluorochemicals are non-yellowing and particularly non-irritating to the skin as well as providing articles that are stable having excellent long term aging properties.

Exemplary fluorochemicals are available commercially from the 3M Company and include ready to use formulations such as Scotchgard TM Fabric Protectors FC-214 and FC-270, Scotch-Release TM Brand Fabric Treatment FC-248, Scotchgard TM Brand Fabric Protector FC-324, 3M TM Brand Textile Chemical FC-461, 3M TM Brand Textile Chemical FC-210, 3M TM Brand Textile Chemical FC-828, 3M TM Brand FC 393, FC 326, FC 905 and FC214B, Scotchgard TM Brand Rain and Stain Repeller FC-232 and the like. Other commercially available materials include Dupont's Soil Shedd TM (available from duPont deNemours and Company, Wilmington, Del.).

Suitable silicones for use to obtain the low surface energy layers of the instant invention include any of the silicones known to those skilled in the art to provide water repellency and optionally oil repellency to fibers and films. Silicone fluids typically consist of linear polymers of rather low molecular weight, namely about 4000–25000. Most commonly the polymers are polydimethylsiloxanes.

For use as fluids with enhanced thermal stability, silicones containing both methyl and phenyl groups are used. Generally, the phenyl groups make up 10–45% of the total number of substituent groups present. Such silicones are generally obtained by hydrolysis of mixtures of methyland phenylchlorosilanes.

Fluids for use in textile treatment may incorporate reactive groups so that they may be cross-linked to give a permanent finish. Commonly, these fluids contain Si-H bonds (introduced by including methyldichlorosilane in the polymerization system) and cross-linking occurs on heating with alkali.

Examples of suitable silicones are those available from Dow-Corning Corporation such as C2-0563 and from General Electric Corporation such as GE-SS4098.

The fluorochemical or silicone which is added to water permeable envelope 2 to impart low surface energy is generally applied at low levels. Suitable amounts are between 0.001 to 0.10 parts by weight of active ingredient per part of fabric or padding. A preferred range is 0.25 to 5.0% by weight, i.e., 0.0025 to 0.050 grams of active ingredient per gram of the envelope.

The curable compound used for impregnating the flexible substrate can be any of the curable compounds known for use in orthopedic applications. Suitable curable compounds include plaster of paris and water-curable prepolymers of polyurethanes, cyanoacrylate esters, and epoxy resins. Particularly preferred curable compounds are isocyanateterminated prepolymers, which are contained in Scotchcast ®2 Brand casting tape.

Figure 2:
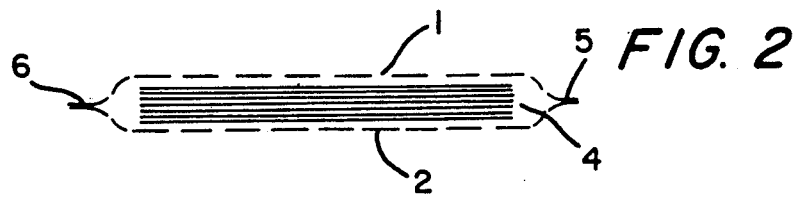
FIG. 2 shows a casting system 1 wherein a resinimpregnated laminate 4 is sealed at the laminate ends 5 and 6 to provide complete enclosure.

In the embodiment shown in FIG. 2, flexible substrate 4 is composed of a plurality of sheets or webs that are impregnated with a curable compound. Also shown in FIG. 2, ends 5 and 6 of envelope 2 are sealed to create a unitary, self-contained orthopedic article. It is also possible and usually preferred to seal the sides of the envelope.

Figure 3:
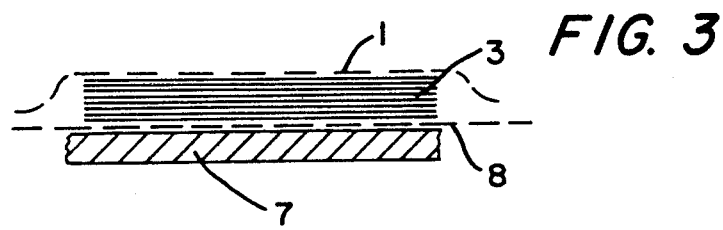
FIG. 3 shows a system wherein a foam layer 7 is applied to one surface 8 of the casting system 1.
Figure 4:
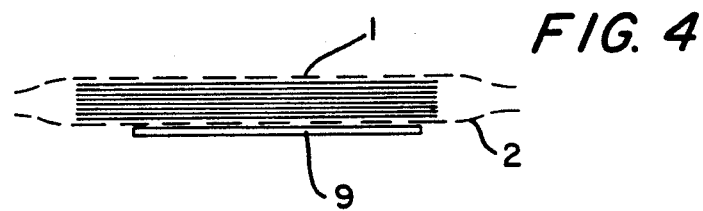
FIG. 4 shows a system wherein a film layer 9 is applied to the surface 2 of a casting system 1.

In the embodiment shown in FIG. 3, a foam layer 7 is applied to one surface of envelope 2. Foam layer 7 is adapted to contact the body part to be immobilized. That is, foam layer 7 acts as a cushion between the body part to be immobilized and member 3. Alternatively a treated foam layer can be included inside the treated fabric envelope. In the embodiment shown in FIG. 4, an impermeable film 9 is provided on one surface of envelope 2. In some instances, it is desirable to keep a surface of the orthopedic article relatively dry. For example, applying a wetted orthopedic article to the area of the body to be immobilized may interfere with medical compositions that have been applied to the body. Impermeable film 9 is provided in order to keep the underlying surface of envelope 2 dry when the orthopedic article is immersed in water to initiate cure.

Figure 5A:
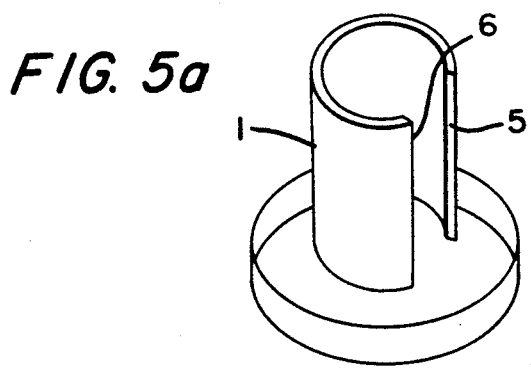
FIG. 5a shows a casting splint 1 formed into a semi-cylinder to be prepared for a porosity test.
Figure 5B:
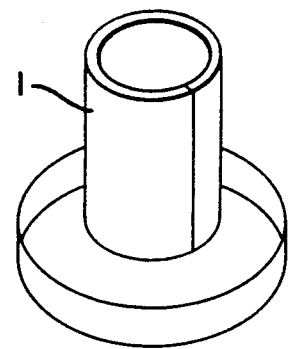
FIG. 5b shows the splint of FIG. 5a formed into a complete cylinder.
Figure 6:
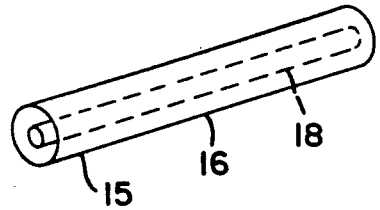
FIG. 6 shows a tubular casting article 15. Cylinders 16 and 18 are covering layers with low surface tension. A casting material is contained between the covering layers.

Splints or casts may partially or totally encompass the body part to be stabilized and protected, and the ends of the splinting article may be joined to form a cylinder, as shown in FIG. 5b. Preformed tubes, such as shown in FIG. 6, are also contemplated in the instant invention.

A further embodiment contemplated is a resin impregnated sheet enclosed between two pieces of open cell foam wherein the foam and/or an adhesive covering one side of the foam is fluorochemically treated.

Various other constructions of articles can be made. There are far too many possibilities available to illustrate them all. The essential element will always be an envelope that possesses a low surface energy and a sufficient porosity to be breathable, yet which contains the casting material without allowing resin leakage.

The method for measuring the surface energy is AATCC Test Method 118-1983, with the modifications described below. Surface energies measured according to this modified test method are hereinafter referred to as "apparent" surface energies. AATCC test method 118-1983 determines the surface energy of a fabric by evaluating the fabric's resistance to wetting by a series of selected hydrocarbon compositions. The hydrocarbons set forth in AATCC 118-1983, however, only provide for measurements of surface energy from about 19.8 to 27.3 dynes per centimeter at 25° C. This range is extended by employing various mixtures of methanol and water in the fabric resistance test. The compositions and their representative surface tensions are as follows.

| Liquid No. | Composition | Surface Tension (dynes/cm at 25° C.) |
|---|---|---|
| 1 | n-heptane | 19.8 |
| 2 | n-octane | 21.4 |
| 3 | n-decane | 23.5 |
| 4 | n-dodecane | 24.7 |
| 5 | n-tetradecane | 26.4 |
| 6 | n-hexadecane | 27.3 |

| Liquid No. | Volume % Methanol/Water | Surface Tension (dynes/cm at 20° C.) |
|---|---|---|
| 7 | 65/45 | 30 |
| 8 | 53/47 | 35 |
| 9 | 40/60 | 40 |
| 10 | 25/75 | 45 |
| 11 | 21/79 | 50 |
| 12 | 15/85 | 55 |
| 13 | 8.5/91.5 | 60 |

| | | |
|---|---|---|
| 14 | 5/95 | 65 |
| 15 | 0/100 | 73 |

The test procedure is as follows. A specimen of the covering material is placed flat on a smooth, horizontal surface. Using the method of AATCC 118-1983 except that beginning with the lowest number test liquid, 5 drops of the liquid are placed on the surface of the fabric on the side which will face the resin impregnated sheet in various locations. If three of the five drops wick into the fabric within 60 seconds, the liquid of the next higher surface energy is used. When at least 3 drops remain on the fabric surface the apparent surface tension is recorded as the range of the last two liquids.

A preferable surface energy has been determined to be about 15 to 40 dynes per centimeter and more preferably less than 30 dynes per centimeter for the tested polyurethane resins.

The liquid curable compound will not leak through the envelope to cause the exterior surface of the article to become sticky or otherwise contaminated with the curable compound. A benefit thus obtained by the orthopedic article of this application is that the curable compound does not leak through the envelope and transfer to the skin of the person who applies the cast and/or the patient, where it could become firmly bonded to the skin.

POROSITY TESTING

An advantage of the orthopedic splinting and casting article of this invention is the high porosity which allows the injured limb to breath. The porosity of the water permeable envelope is tested using a W & L.E. Gurley Densometer Model 4110. (Troy, N.Y.). A Gurley-Teledyne sensitivity meter (Cat. No. 4134/4135) is used (only for calibration). An Engler Instruments Co. Model 605 timer is used to record the porosity as the time in sec. to pass 100cc of air through a 1.128" diameter (1.000 sq. in) piece of the envelope at 74°-76° F. and 50% relative humidity. Both single and double layers are tested in some cases. The results appear below:

POROSITY

| Envelope Material (sec) | Single layer (sec) | Double layer |
|---|---|---|
| Elastoflex P, 1.5 mil thickness | Greater than 300 secs (almost no flow) | |
| Adhesive-backed polyurethane foam | 10.5 | |
| MSO3 | 0.2 | 0.3 |
| MSO3 containing 2.5% FC-270 | 0.2 | 0.25 |
| MSO3 containing 0.5% FC-214 | 0.3 | 0.8 |
| MSO3 containing 0.25% FC-214 | 0.3 | 0.7 |
| MSO3 containing 1.0% FC-214 | 0.25 | 0.6 |
| MSO3 containing 2.0% FC-214 | 0.3 | 0.8 |
| MSO3 containing 2.5% FC-461 | 0.2 | 0.5 |
| MSO3 containing 2.5% FC-828 | 0.25 | 0.7 |
| MSO3 containing 0.25% FC-232 | 0.25 | 0.9 |
| MSO3 containing 0.50% FC-232 | 0.25 | 0.7 |
| MSO3 containing 2.5% FC-210 | 0.3 | 0.65 |

POROSITY-continued

| Envelope Material (sec) | Single layer (sec) | Double layer |
|---|---|---|
| FC-214 Splint | 1.3 | — |

Elastoflex P is a proprietary elastomeric film, available from Clopay Company, Cincinnati, Ohio. MSO3 is the knitted polyester stockinette onto which all the fluorochemicals listed were coated. The percentage refers to % by weight of the fluorochemical which was coated onto the MSO3 knitted polyester stockinette available from 3M Company, St. Paul, Minn. FC-214 Splint is eight layers of Scotchcast TM 2 casting tape enclosed in MSO3 treated with 2% FC-214.

WATER VAPOR POROSITY

A casting splint consisting of eight layers of Scotchcast TM 2 casting tape material impregnated with a water curable urethane prepolymer and enclosed on all sides by an envelope is formed into a cylinder of two inches inner diameter and three inches in height as shown in FIGS. 5a and 5b and by sealing the ends 5 and 6 together using a room temperature vulcanizing silicone adhesive such as Dow Corning 732 multipurpose sealant. The envelope totally encases the water-curable casting material and is therefore present on both the inner and outer surfaces of the cylinder which has been formed. In Sample 1, the envelope consists of an ethylene-propylene-diene film. Sample 1 is currently sold under the name Scotchcast TM 2 Splinting System by 3M Company. In Sample 2, the envelope consists of a polyester stockinette that is treated to contain 1.25% by weight of FC-214 fluorochemical. In Sample 3, the envelope consists of a first layer of polyester stockinette and a second layer over the outside of the cylinder of an open cell urethane foam adhered to the first layer by the adhesive backing. This envelope is also treated on the stockinette portion to contain 1.25% by weight of FC-214 fluorochemical. In Sample 4, the envelope consists of a polyester stockinette treated to contain 2.5% by weight of FC-214 fluorochemical.

A beaker containing water is sealed inside the cylinder by placing a Petri dish 10 at the open bottom and top of the cylinder and gluing the dishes to the splint using a room temperature vulcanizing silicone adhesive as described hereinabove. After the adhesive is cured, this assembly is placed in a 90° to 100° F. (32° to 38° C.) oven and weight loss of the assembly is measured as a function of time. The weight loss of the assemblies containing fabric treated with fluorochemical (Samples 2-4) is compared to an assembly in which the film was not treated with fluorochemical (Sample 1). The properties of Samples 1-4 are shown in Table 1.

TABLE 1

| Sample | % Fluorochemical added (by weight) | Surface tension (dynes/cm) |
|---|---|---|
| 1 | 0 | not applicable |
| 2 | 1.25 | 23.5-24.7 |
| 3 | 1.25 | 23.5-24.7 |
| 4 | 2.5 | 21.4-23.5 |

Figure 8:
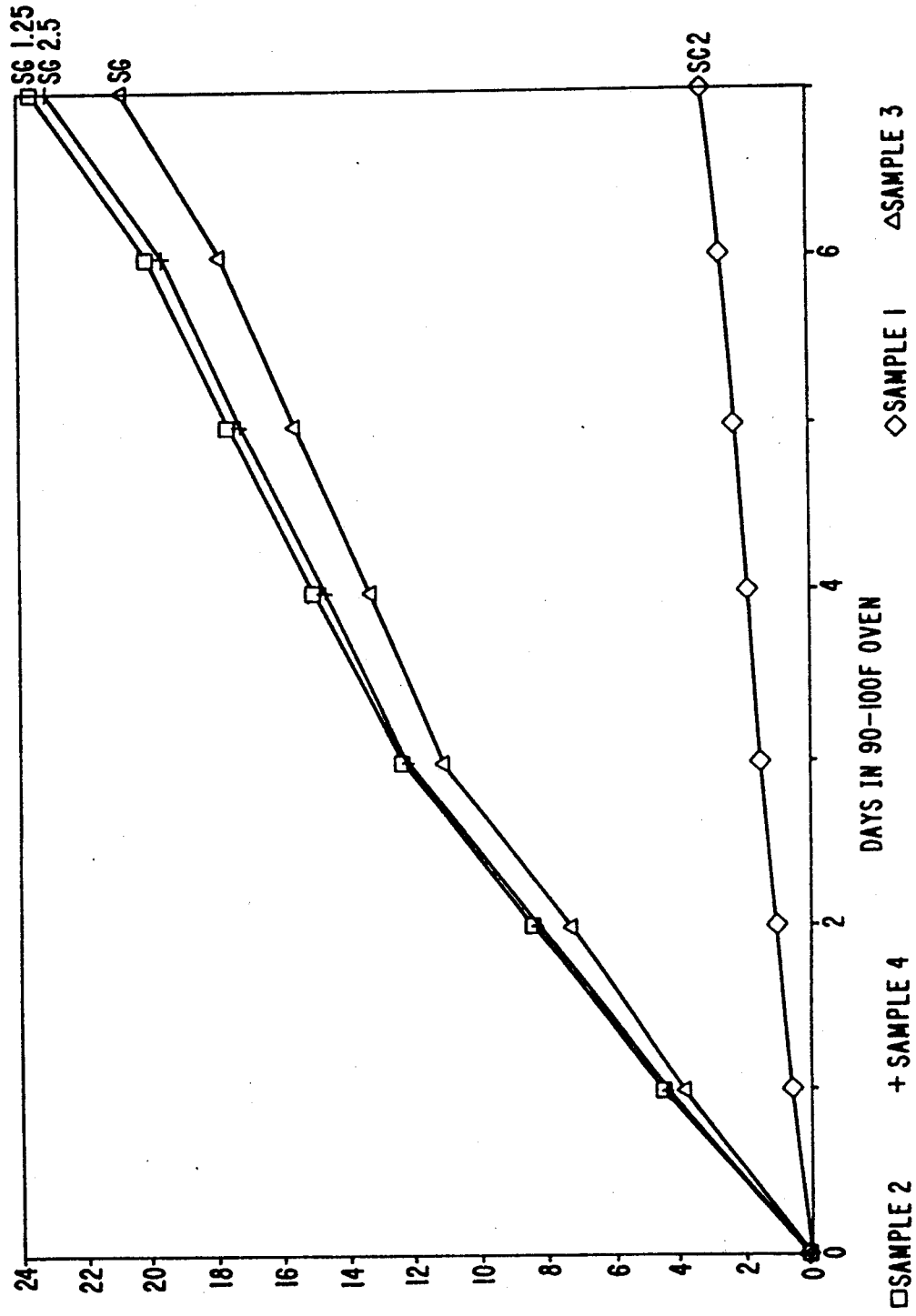
FIG. 8 shows water transport through treated and untreated orthopedic articles in grams per day.

The results of the water vapor porosity test are shown in FIG. 8. FIG. 8 shows the grams of water vapor that are transported through the splints as a function of time. As indicated in the figure, Samples 2-4, which are porous fabrics treated with fluorochemical, transport water much more rapidly than Sample 1.

The following examples are provided to illustrate the invention and should not be considered as restrictive.

EXAMPLE 1

Figure 7:
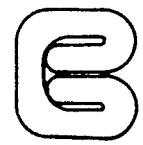
FIG. 7 shows schematically the article of FIG. 6 folded for storage.

Tubular samples of about 15 inches in length and 3 inches in diameter of 3M ™ Brand MSO3 polyester stockinet are treated with the fluorochemical formulations as listed in Table 2. The wet pick-up of a solution diluted to 2.5% solids using deionized water is between 100 and 120% by weight. Percent wet pickup is weight of a wet stockinet divided by weight of a dry stockinet multiplied by 100. Each treated stockinet is heated for one hour in an oven at 300° F. (149° C.) and stored in a dry chamber (4% relative humidity) at a constant temperature of 24° C. for about three days. Each sample contains about 2.5% by weight of the fluorochemical. These are tested by the modified version of AATCC Test Method 118-1983 described above for apparent surface energy and the results are reported in Table 2. The color of each sample is recorded. Eight layers, each 12 inches (30.5 cm) in length and 3 inches wide of Scotchcast ™ 2 Brand casting tape (a product described in U.S. Pat. No. 4,609,578, incorporated herein by reference, and available from 3M Company, St. Paul, Minn.) made with an isocyanate functional water curable resin were enclosed in the treated tubular stockinet. The ends of the tube are placed in apposition and carefully heat sealed with a Vertrod Mead Model 14A-A-CAB Sealer. The casting articles were folded as shown in FIG. 7, packaged and sealed in aluminum foil pouches and aged at 120° F. (49° C.). After two weeks the pouches were opened and the aged articles were inspected visually for color and manually for the presence of resin on the outer fabric surface. The results are shown in Table 2.

TABLE 2

| Run No. | Fluorochemical Treatment | Color of Treated Stockinet | Description of Aged Articles | Apparent Surface Energy Range (dyne/cm) |
|---|---|---|---|---|
| A | FC-214 | No Change | No resin leakage | 21.4–23.5 |
| B | FC-210 | No Change | No resin leakage | 21.4–23.5 |
| C | FC-232 | No Change | No resin leakage | 21.4–23.5 |
| D | FC-828 | Slight Yellowing | No resin leakage | 23.5–24.7 |
| E | FC-461 | Slight Yellowing | No resin leakage | 21.4–23.5 |
| F | untreated | Not Applicable | Visible wet out/sticky | >72 |

This example shows that with the specific stockinet and resin used, three completely satisfactory fluorochemical treatments were found.

EXAMPLE 2

Samples of 3M ™ Brand MSO3 polyester stockinet and commercially available cotton stockinet are treated with 1.5% and 2.5% by weight total solids aqueous solution of FC-214. This is supplied as a 30% solids solution, and hence can be diluted to obtained the desired solids content. A wet pickup of 45% was obtained for the 3 inch (7.6 cm) diameter cotton stockinet cylinder. The wet pickup is controlled by passing the soaked materials through a set of nip rollers. The stockinet samples are soaked in the solutions, then dried by hanging in a convection oven at 320° F. (160° C.) for 40 minutes. The surface tension of the outside and inside surface of each stockinet is qualitatively evaluated visually after applying water and modified diphenylmethane, available from Dow Chemical under the name Isonate ™ 143L. Both the inside and outside surfaces repelled these chemicals, i.e., droplets of these liquid chemicals remained beaded up on the surface and did not wick into the fabric. Untreated samples were wetted by both water and Isonate 143L.

EXAMPLE 3

Samples of nonwoven sheets of commercially available spun-laced, hydroentangled nonwoven polyester fabrics Sontara 8000, 8005 and 8010 (available from du Pont, Wilmington, Del.) are treated with commercially available FC-214. The FC-214 is diluted to 2% solids with water. The fabrics are soaked in the solution, run through a nip roller, resoaked, and again run through the nip roller to provide a substantially uniform 100% wet pickup. Untreated samples are soaked in water. All of the samples are dried as described in Example 2 and the surface tension of each sample qualitatively tested as in Example 2. The treated samples have significantly reduced surface tension compared to the untreated samples. This is shown by the fact that water and Isonate ™ 143L would not wet the treated fabric but the untreated fabric is wetted. Splints are made from these samples and described in Example 1 and are aged at 100° F. (24° C.) for 2 months without any detectable resin leakage. Control samples which were not treated showed visible resin wet-out after 4 weeks and were sticky.

EXAMPLE 4

Two casting splints 3 inches in width are made using a commercially available polyethylene terephthalate terry cushion stockinet (available from Balfour, Inc., Rockwood, Tenn.) treated with a solution of FC-214 diluted to 2.5% solids (120% pickup) to encase eight layers of Scotchcast ™ 2 Brand Casting Tape. The ends of the stockinets are heat sealed to form a complete closure. One side of each splint is covered with a 3 inch wide strip of water-impervious Scotch ™ Brand polyester tape No 355-G clear tape (available from 3M Company, St. Paul, Minn.). The splints are dipped in water to initiate curing, removed from the water, then the vinyl tape is removed to expose a dry surface. The dried surface is applied to the skin and is comfortable and not damp.

EXAMPLE 5

Two casting splints 3 inches in width and 14 inches long are made using the stockinet material and casting tape of Example 4 which are heat sealed. A 3 inch wide, 3/16 inch thick strip of adhesive backed polyurethane foam of equal length to the splint is glued at each end to the ends of the splint with 3M ™ brand hot melt adhesive. The splint is dipped in water while holding the foam section of the splint out of the water. The splint is removed from the water. Excess water is removed by hand squeezing, the adhesive side of the foam is applied to the splint and the dry foam side of the assembly is applied to the skin as the assembly is used as a splint. The skin area is comfortable and not damp.

EXAMPLE 6

In order to obtain quantitative measurements of the repellency of treated stockinets of the instant invention, 3 inch wide and 2 inch long sections of treated fabrics which are made by the method of Example 1 are evaluated using the modified version of AATCC Test Method 118-1983 described above for apparent surface energy as shown in Table 3.

TABLE 3

| Run | Stockinet Fabric Treatment* | Surface Energy Range (Dynes/cm) |
| --- | --- | --- |
| 1A | FC 232, 0.25% | 27.3 to 29.6 |
| 2A | FC 232, 0.50% | 26.4 to 27.3 |
| 3A | FC 232, 1.0% | 23.5 to 24.7 |
| 4A | FC 232, 2.0% | 21.4 to 23.5 |
| 5A | FC 214, 0.25% | 24.7 to 26.4 |
| 6A | FC 214, 0.50% | 24.7 |
| 7A | FC 214, 1.0% | 23.5 to 24.7 |
| 8A | FC 214, 2.0% | 21.4 to 23.5 |
| 9A | Dow C 20563 Silicone, 2% | Between 27.3 and 30 |
| 10A | General Electric 5540 98 Silicone, 2.4% | Between 27.3 and 30 |
| 11A | Orthoglass Rollform Splint | greater than 72** |
| 12A | Untreated Stockinet | greater than 72** |
| 13 | FC 270, 25% | 24.7 to 26.4 |

*All percents are grams of solid per gram of fabric times 100
**wetted by distilled water Runs 9A and 10A provided splints which yellowed. After one week aging at 120° F. neither splint showed resin leakage. After 19 days at 120° F. splint 9A was not sticky but splint 10A was sticky.

What is claimed is:

1. An orthopedic article adapted to immobilize a body part, comprising (a) a flexible substrate having opposing surfaces impregnated with a curable liquid compound, and (b) a cover disposed on the surfaces that is permeable to water and impermeable to the curable liquid compound, said cover comprises a flexible sheet treated with a material selected from the group consisting of a fluorochemical and a silicone.

2. The article of claim 1, wherein the cover has an apparent surface energy of less than about 30 dynes per centimeter and a porosity of less than about 10.5 seconds.

3. The article of claim 2, wherein the cover comprises a knitted, woven, or a non-woven fabric treated with the material disposed on one of the opposing surfaces and a foam treated with the material disposed on the other opposing surface.

4. The article of claim 1, wherein the cover comprises a knitted, woven, or a non-woven fabric or foam treated with the material.

5. The article of claim 4, wherein the fabric is treated with a fluorochemical.

6. The article of claim 4, wherein the fabric is treated with a silicon.

7. The article of claim 4, wherein the curable compound is a water-curable isocyanate-terminated prepolymer resin.

8. The article of claim 4, wherein the amount of the material is from 0.01 to 10% by weight of the fabric.

9. The article of claim 4, wherein the amount of the material is from 0.25 to 5% by weight of the fabric.

10. The article of claim 1, further comprising a foam layer disposed on a side of the cover opposing one surface of the substrate, wherein said foam layer is adapted to contact the body part to be immobilized.

11. The article of claim 1, wherein the cover comprises a sealed envelope encasing the substrate.

12. The article of claim 1, wherein the apparent surface energy of the cover ranges from 15 to 40 dynes per centimeter and the cover has a porosity of less than about 10.5 seconds.

13. The article of claim 1, wherein the flexible sheet is a laminate comprising a treater layer adjacent to the flexible substrate and treated with the material, and at least one other layer, wherein the treated and other layers are selected from the group consisting of a woven web, a non-woven web, a knitted web and a foam.

14. The article of claim 1, wherein the cover has a porosity of about 1.0 second or less.

15. The article of claim 1, wherein the cover comprises a knitted, woven, or a non-woven fabric treated with the material disposed on one of the opposing surfaces and a foam treated with the material disposed on the other opposing surface.

16. The article of claim 1, wherein the cover comprises a knitted, woven, or a non-woven fabric treated with the material disposed on one of the opposing surfaces and adhesively attached to a foam treated with the material such that the cover forms an envelope encasing the flexible substrate.

17. The article of claim 1, in the form of a kit further comprising a separate cushion adapted to contact a body part to be immobilized and wherein the cover comprises a knitted, woven, or a non-woven fabric treated with material.

18. A method of making an orthopedic article adapted to immobilize a body part comprising the steps of (a) impregnating a flexible substrate having opposing surfaces with a curable liquid compound, and (b) applying to the surfaces a cover comprising a flexible sheet that has been treated with a material selected from the group consisting of a fluorochemical and a silicone, that is permeable to water and impermeable to the curable liquid compound.

19. A method of immobilizing body part comprising the steps of (a) activating the curable liquid compound in the article of claim 1, (b) applying the article of claim 1 to the body part, and (c) allowing the curable liquid compound to cure.

20. The method of claim 19, wherein the curable compound is activated by soaking the article in water.

* * * * *

UNITED STATES PATENT AND TRADEMARK OFFICE
CERTIFICATE OF CORRECTION

PATENT NO.  : 5,027,803
DATED       : July 2, 1991
INVENTOR(S) : Matthew T. Scholz et al.

It is certified that error appears in the above-identified patent and that said Letters Patent is hereby corrected as shown below:

Col. 1, line 53, "resinimpregnated" should be --resin-impregnated--.

Col. 2, lines 11 and 12, "resinimpregnated" should be --resin-impregnated--.

Col. 2, lines 13 and 14, "resinim-pregnated" should be --resin-impregnated--.

Col. 5, line 42, "methyland" should be --methyl- and--.

Col. 6, line 61, "Tension" should be --Tension*--.

Col. 7, line 4, after the table, please insert --*interpolated from Handbook of Chemistry and Physics, 56th Edition, CRC Press, pp. F-42 and F-43.--

Col. 12, line 4, "silicon" should be --silicone--.

Col. 12, line 23, "treater" should be --treated--.

Col. 12, line 56, after "immobilizing" insert --a--.

Signed and Sealed this

Twenty-ninth Day of December, 1992

*Attest:*

DOUGLAS B. COMER

*Attesting Officer*     Acting Commissioner of Patents and Trademarks